United States Patent [19]

Hiraki et al.

[11] Patent Number: 5,294,552
[45] Date of Patent: Mar. 15, 1994

[54] STRAIN MASS-PRODUCING ε-POLY-L-LYSINE

[75] Inventors: Jun Hiraki; Hiroshi Morita, both of Yokohama, Japan

[73] Assignee: Chisso Corp., Osaka, Japan

[21] Appl. No.: 864,183

[22] Filed: Apr. 3, 1992

Related U.S. Application Data

[63] Continuation-in-part of Ser. No. 568,658, Aug. 14, 1990, abandoned, which is a continuation of Ser. No. 81,405, Jul. 31, 1987, abandoned.

[30] Foreign Application Priority Data

Aug. 19, 1986 [JP] Japan ................ 61-192157
Aug. 19, 1986 [JP] Japan ................ 61-192158

[51] Int. Cl.$^5$ ............ C12N 1/20; C12N 15/00
[52] U.S. Cl. .............. 435/252.3; 435/172.1; 435/172.3; 435/71.2; 435/252.35
[58] Field of Search ........... 435/172.1, 172.3, 252.3, 435/71.2, 252.35

[56] References Cited

U.S. PATENT DOCUMENTS 4,411,991 10/1983 Hirakawa et al. ........... 435/106

FOREIGN PATENT DOCUMENTS 072896 6/1978 Japan ........... 435/115
59-20359 7/1984 Japan .

OTHER PUBLICATIONS

Maniatis et al, *Molecular Cloning* ... pp. 313, 88 1982.

*Primary Examiner*—Irene Marx
*Attorney, Agent, or Firm*—Browdy and Neimark

[57] ABSTRACT

The present invention provides mutants mass-producing εPL which are obtained by mutation treatment of a strain producing εPL. For using the mutants, the mutants are cultured in a cultivated medium, εPL is mass-produced and stored in the culture solution, and the stored εPL is collected from the solution. For producing εPL, a strain which produces εPL is mutation-treated, the obtained mutant is cultivated in a culture medium to which L-lysine or L-lysine and one or more sugars are added, εPL is mass-produced and stored in the culture solution, and the stored εPL is collected from the solution.

The mutants producing εPL in large quantities are preferably the mutants which have tolerance to an analogue of L-lysine of *Streptomyces albulus* subsp. lysinopolymerus No. 346-D strain and chloramphenicol-treated mutant of the same bacteria.

2 Claims, No Drawings

STRAIN MASS-PRODUCING ε-POLY-L-LYSINE

This application is a Continuation-in-part of application Ser. No. 07/568,658, filed Aug. 14, 1990, which is a continuation of application Ser. No. 07/081,405, filed Jul. 31, 1987, both now abandoned.

BACKGROUND OF THE INVENTION

This invention relates to a mutant which mass-produces ε-poly-L-lysine (abbreviated as εPL in the following), a method for using the mutant and a method for producing εPL. εPL is a high-molecular weight compound as described in the following equation in which amino groups of ε-positions of L-lysine are linked to adjacent carboxyl groups of L-lysine by amide bond formation.

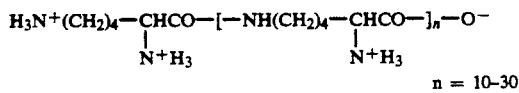

$$n = 10\text{-}30$$

As this material is a polymer of L-lysine which is an essential amino-acid, it has high safety and peculiar physical properties because of its high cation content. Accordingly, its utility in toiletry supplies, beauty aids, feed additives, pharmaceuticals, agricultural medicines, food additives, electronic materials, etc. is evident, give by using these properties.

Hitherto, this material was obtained by cultivating the strain of *Streptomyces albulus* subsp. lysinopolymerus No. 346-D (deposit No. 3834 of microorganisms of FRI) which is a εPL production bacterium belonging to Streptomyces in a culture medium, separating it from the obtained culture materials and refining it (Japanese Patent Publication 59-20359).

However, εPL was produced at most 0.5 g per liter of culture solution from the said strain. Accordingly, the production cost of this material was high and its wide utilization was prevented.

The inventors of the present invention have obtained a mutant mass-producing εPL, investigated repeatedly in order to produce εPL in large quantities by using the said mutant, and attained the following invention.

SUMMARY OF THE INVENTION

The present invention provides a mutant mass-producing εPL which is obtained by mutation treatment of a mutant producing εPL. Further, the present invention provides a method for using the mutant, characterized in that the mutant is cultured in a cultivated medium, εPL is mass-produced and stored in the culture solution, and the stored εPL is collected from the solution. The present invention also provides a method for producing εPL, characterized in that a mutant which produces εPL is mutation-treated, the obtained mutant is cultivated in a culture medium to which L-lysine or L-lysine and one or more sugars are added, εPL is mass-produced and stored in the culture solution, and the stored εPL is collected from the solution.

The mutant is a mutant which produces εPL in large quantities, preferably it is a mutant which has tolerance to an analogue of L-lysine of *Streptomyces albulus* subsp. lysinopolymerus No.346-D strain or a chloramphenicol-treated mutant of the same bacterium.

The analogue material of L-lysine is preferably S-aminoethyl-L-cysteine or a mixture of S-aminoethyl-L-cysteine and one or more materials selected from the group of L-threonine, glycine, L-homoserine and L-methionine.

Further, the chloramphenicol-treated mutant of *Streptomyces albulus* subsp. lysinopolymerus No.346-D strain is a strain which is obtained by chloramphenicol treatment, and a chloramphenicol-treated mutant 50833 strain (deposit No.1110 of microorganisms of FRI) obtained by chloramphenicol treatment can be exemplified.

The following description serves to illustrate the invention more specifically.

Firstly, a method for obtaining the mutants of the present invention is described. The mutants which have tolerance to an L-lysine analogue such as S-aminoethyl-L-cysteine are prepared, e.g., from the following method.

Spores of *Streptomyces albulus* subsp. lysinopolymerus No.346-D strain are suspended in trismaleic acid buffer solution (pH 9.0) and N-methyl-N-nitro-N'-nitrosoguanidine is added to the solution.

After shaking the solution, the spores are collected by centrifugation, washed with sterilized water and inoculated in a culture medium. By shaking the medium, bacteria are cultivated. The culture medium containing the bacteria (hereinafter the medium is referred to as culture solution) is diluted. Then, S-aminoethyl-L-cysteine or a mixture of S-aminoethyl-L-cysteine and one or more materials selected from the group of glycine, L-threonine, L-homoserine and L-methionine is added to an agar culture medium having the same composition as the above medium.

In this case, S-aminoethyl-L-cysteine in concentration from 0.5 to 10 mg per ml of the agar culture medium, preferably 2mg, or a mixture of S-aminoethyl-L-cysteine in the same concentration and one or more amino acids selected from the above group in concentration from 0.2 to 5 mg per ml of the agar culture medium, preferably 1 mg, is usable. The above diluted culture solution is applied to this agar culture medium. After incubating the applied agar culture medium, S-aminoethyl-L-cysteine mutants are obtained as colonies. The mutant cultivated in the agar culture medium containing S-aminoethyl-L-cysteine alone is a tolerant mutant 81512 strain. The mutant cultivated in the agar culture medium containing S-aminoethyl-L-cysteine and glycine is a tolerant mutant 11011A-1 strain (deposit No.1109 of microorganisms of FRI). Further, the mutant cultivated in the agar culture medium containing S-aminoethyl-L-cysteine and L-threonine is a tolerant mutant 81502 strain. Fermentation Research Institute an Agency of Industrial Science and Technology, Ministry of International Trade and Industry, is located 1-3, Yatabemachi Higashi 1 Chome, Tsukubaun, Ibarakiken, Japan 305.

Next, the chloramphenicol-treated mutants are obtained by chloramphenicol treatment, e.g., by the following method. *Streptomyces albulus* subsp. lysinopolymerus No.346-D strains or S-aminoethytl-L-cysteine tolerant mutant is inoculated in a culture medium. After shaking the medium, chloramphenicol is added to the medium, and cultivation is continued. Cultivated bacteria are collected by centrifugation, washed, and applied to an agar culture medium. After static cultivation, a conventional agar culture medium containing *Staphylococus aureus* is overlapped on the said medium. After further cultivation, the strains which formed a large zone of inhibition of growth of

*Straphylococcus aureus* are the desired chloramphenicol-treated mutant 50833 strain (deposit No.1110 of microorganisms of FRI). Among these mutants, the mycological properties of the 11011A-1 strain and the 50833 strain are as follows.

1. Morphological properties:

Aerical Mycel and Substrate Mycelium of the 11011A-1 mutant and the 50833 strain which were grown on a sucrose-nitrate agar culture medium at 30° C. for ten days were observed by a microscope. The result is as follows.

1) Ramification and morphology of the sporogenesis mycelia: simple ramification, and closed spiral.

2) Spore number: several tens.

3) Surface structure and spore size: spiny, about 1.2–1.5μ, and round or oval shape.

4) Existence of flagellum spores, bacterium nucleuses and sporangia: non.

5) Insertion position of Sporophore: on Aerical Mycel.

2. Growth conditions on various culture mediums

Properties of the mutants on the following various culture mediums are shown as observation results after cultivating at 30° C. for 10–14 days.

a) The 11011A-1 strain
(deposit No. 1109 of microorganisms of FRI)

| Culture midium | Substrate Mycelium | Aerical Mycel | Soluble pigment |
| --- | --- | --- | --- |
| Sucrose-nitrate agar | pale yellow | gray brown | non |
| Glucose-asparagine agar | pale yellow | white, powdery | pale yellow |
| Glycerol-asparagine agar | pale yellow, then, yellow brown | bad growth of Aerical Mycel | pale yellow |
| Tyrosine agar | pale brown | white, rich, powdery | brown |
| Nutrient agar | pale yellow | white, rich | non |
| Yeast-maltose agar | pale yellow wrinkled | white, powdery, gray brown spots | non |
| Oatmeal agar | pale gray | white, then, gray brown | non | b) The 50833 strain (deposit No. 1110 of microorganisms of FRI)

| Culture midium | Substrate Mycelium | Aerical Mycel | Soluble pigment |
| --- | --- | --- | --- |
| Sucrose-nitrate agar | pale yellow | gray brown | non |
| Glucose-asparagine agar | pale brown | white, powdery | pale yellow |
| Glycerol-asparagine agar | pale yellow, then, yellow brown | bad growth of Aerical Mycel | pale yellow |
| Tyrosine agar | brown | white, powdery, rich | brown |
| Nutrient agar | pale yellow | white, rich | non |
| Yeast-maltose agar | pale yellow wrinkled | white, powdery, gray brown spots | non |
| Oatmeal agar | pale gray | white, then, gray brown | non |

3. Physiological properties

The physiological properties of the 11011A-1 strain and the 50833 strain are as follows.

1) Range of growth temperatures: about 15°–40° C. The optimum growth temperature: about 30° C.

2) Liquefaction of gelatine, hydrolysis of starch and peptonization of skin milk: all positive.

3) Coagulation of skin milk: negative.

4) Formation of melaninlike pigments: a brown pigment is produced on the tyrosine agar culture medium.

5) Composition of cell walls: the analytical result obtained by the method of Becker et al. (Applied Microbiology, 13, 236 (1965)) shows that the type of diaminopimelic acid in the composition of cell walls was L, L type.

4. Assimilability of various carbon sources on the Pridham Gottliep agar culture medium:

| | |
| --- | --- |
| L-arabinose | – |
| D-xylose | – |
| D-glucose | + |
| D-fructose | + |
| L-rhamnose | – |
| D-galactose | + |
| sucrose | – |
| raffinose | – |
| D-mannitol | + |
| i-inositol | + |
| salicin | – | notes:
+: assimilate
–: dissimilate

As described above, the properties of the mutants of the present invention are similar to the properties of *Streptomyces albulus* subsp. lysinopolymerus No.346-D strain which is an original strain.

Then εPL is prepared by the present invention using the mutants obtained by the above described methods. Further, % in this specification indicates weight(g)-/volume(ml) % unless otherwise noted.

Firstly, the obtained mutants are inoculated in a culture medium, e.g., adding L-lysine or L-lysine and one or more sugars, and cultivated. The εPL obtained from the culture medium containing the culture materials (abbreviated as culture solution hereinafter) is separated and purified. Any culture mediums containing carbon sources, nitrogen sources, inorganic salts and vitamin can be used. Although not limiting, a medium containing 5% of glucose or 5% of glycerin as the carbon source, and ammonium sulfate, L-lysine or peptone as the nitrogen source is preferred. In the course of the cultivation, the carbon source and the nitrogen source can be added successively or continuously to the culture medium.

When L-lysine and sugars are added to the culture solution, L-lysine and sugars can be added anytime from the beginning to the ending of the cultivation, preferably in the middle of the cultivation when pH is falling. As the form of L-lysine to be added, L-lysine monohydrochloride can be used in the range of 0.05–2% based on the total volume of the culture solution, preferably 0.5%. For the sugars, one or more sugars selected from the group of glucose, sucrose, maltose, starch, galactose, etc., and glycerine can be used in the range of 0.5–5% based on the total volume of the culture solution, preferably 2.5% of glucose can be used.

In succesive addition, L-lysine and sugars are added when the sugar concentration in the culture solution is falls below a fixed %. For example, 2.5% of glucose and 0.5% of L-lysine are preferably added when the sugar concentration is falls below 0.1%.

In continuous addition, a glucose solution and an L-lysine solution can be passed through a culture tank and the culture solution can be eliminated so as to maintain, for example, the glucose concentration, e.g., at 1% and, for example, L-lysine concentration, e.g., at 0.2% in the culture solution. Further, a defoaming agent can be added to the culture solution.

The pH value can be allowed to fall up to 4.0 at the beginning of the cultivation, and then maintained at 4.0 by adding an alkali solution such as an aqueous sodium hydroxide solution. After removing the cultivated bacteria with a centrifuge or a filter from the culture solution, the filtrate is purified, decolorized and concentrated. εPL is crystallized out of the concentrated solution by using an organic solvent such as acetone, ethanol, etc.

The effects of the present invention are as follows.

The mutants of the present invention have the ability to mass-produce εPL. By cultivating the said mutants, the mutants produce more εPL than the known strains. Further, according to the present invention, when the mutants of the strains producing εPL are cultivating, the mutants can produce εPL in large quantities by adding L-lysine or L-lysine and one or more sugars to the culture solution.

Accordingly, the production cost of εPL can be greatly lowered in comparison with the conventional methods.

DESCRIPTION OF THE PREFERRED EMBODIMENTS

The following non-limiting examples illustrate the present invention more specifically.

EXAMPLE 1

Obtention of Mutants Tolerant to S-aminoethyl-L-cysteine

Spores of *Streptomyces albulus* subsp. lysinopolymerus No.346-D strain in quantities of a platinum earpick were suspended in tris-maleic acid buffer solution (pH 9.0) and N-methyl-N-nitro-N'-nitrosoguanidine was added to the solution. After shaking the solution at 30° C. for 30 minutes, the spores were collected with a centrifuge, washed with sterilized water and inoculated in 5 ml of the culture medium of pH 6.8 that contains 5% of glucose, 1% of ammonium sulfate, 0.5% of yeast extract, 0.136% of potassium dihydrogen phosphate heptahydrate, 0.158% of disodium hydrogen phosphate dodecahydrate, 0.05% of magnesium sulfate heptahydrate, 0.004% of zinc sulfate heptahydrate, 0.003% of ferrous sulfate heptahydrate (the medium is abbreviated as the first culture medium hereinafter). By shaking cultivation at 30° C. for a whole day and night, bacteria were grown.

The culture solution was diluted 5000-fold by adding the MS solution which contains of 0.05% of magnesium sulfate heptahydrate, 0.5% of sodium chloride and 0.05% of Tween 80 (Trade mark). Then, the diluted culture solution was applied to the agar culture medium having the same component as that of the first culture medium in addition to S-aminoethyl-L-cysteine or S-aminoethyl-L-cysteine in concentration of 2 mg per ml of the agar culture medium and glycine or L-threonine in concentration of 1 mg per ml of the agar culture medium. The applied agar culture medium was incubated at 30° C. for 48 hours to grow mutants as colonies, and mutants tolerant to S-aminoethyl-L-cysteine were obtained.

In this case, the mutant obtained from the agar culture medium to which only S-aminoethyl-L-cysteine was added, was the 81512 strain. The mutant obtained from the agar culture medium to which S-aminoethyl-L-cysteine and glycine were added, was the 11011A-1 strain (deposit No.1109 of microorganisms of FRI). The mutant obtained from the agar culture medium to which S-aminoethyl-L-cysteine and L-threonine were added, was the 81502 strain.

Production of εPL

S-Aminoethyl-L-cysteine tolerant 81512 strain in quantities of a platinum earpick was inoculated in 5 ml of the culture medium having the same composition as that of the above first culture medium, cultivated with shaking at 30° C. for eight days. At the conclusion of the cultivation, the concentration of εPL in the culture solution was determined by the method of Itzhaki.

The yield of εPL per liter of the culture solution was 0.67 gr.

EXAMPLES 2 AND 3

Using the same method as used in Example 1 except that the mutant 81512 strain tolerant to S-aminoethyl-L-cysteine was changed to the mutant 11011A-1 strain tolerant to S-aminoethyl-L-cysteine and glycine (deposit No. 1109 of microorganisms of FRI) (Example 2) and the mutant 81502 strain tolerant to S-aminoethyl-L-cysteine and L-threonine (Example 3), εPL was produced and its concentration was determined by the same method as in Example 1.

The yields of εPL per liter of the culture solution were 0.88 gr.(Example 2) and 0.72 gr.(Example 3), respectively.

EXAMPLE 4

Obtention of the Chlorampherical-treated Mutants

The mutant tolerant to S-aminoethyl-L-cysteine that was obtained in Example 1 was inoculated in 5 ml of the culture medium having the same composition as that of the first culture medium as described in Example 1.

After shaking the culture medium at 30° C. for two days, chloramphenicol in quantities from 50 to 500 mg per liter of the culture solution, preferably 100 mg, was added to the solution, and the cultivation was continued for another 5–10 hours, preferably eight hours. The cultivated bacteria were collected by centrifugation, washed with sterilized water or a physiological saline solution and applied to an agar culture medium having the same composition as that of the first culture medium in addition to 1.7% of agar.

After static cultivation at 30° C. for 8 days, a conventional agar culture medium containing Staphylococcus aureus was overlapped on the said medium. After cultivating further one night, the strains which formed large zone of inhibition of the growth of *Staphylococcus aureus* were the desired chloramphenicol-treated mutant 50833 strain (deposit No.1110 of microorganisms of FRI).

Production of εPL

Using the same method as described in Example 1 except that the 81512 strain was changed to the obtained 50833 strain, εPL was produced and its concentration was determined by the same method as in Example 1.

The yield of εPL per liter of the culture solution was 1.80 gr.

COMPARISON EXAMPLE 1

Using the same method as described in Example 1 except that mutant of the mutant 81512 strain tolerant to S-aminoethyl-L-cysteine was changed to *Streptomyces albulus* subsp. lysinopolymerus No.346-D strain, εPL was produced and its concentration was determined by the same method as in Example 1.

The yield of εPL per liter of the culture solution was 0.20 gr.

EXAMPLE 5

Using the same method as described in Example 4 except that the production of εPL was conducted as follows.

The chloramphenicol-treated mutant 50833 strains in quantities of a platinum earpick were inoculated in 5 ml of the culture medium having the same composition as that of the above culture medium with the addition to 0.5% of L-lysine monohydrochloride, and were cultivated with shaking at 30° C. for eight days. At the conclusion of the cultivation, the concentration of εPL in the culture solution was determined by the method of Itzhaki.

The yield of εPL per liter of the culture solution was 1.85 gr.

COMPARISON EXAMPLE 2

Using the same method as described in Example 5 except that the chloramphenicol-treated mutant 50833 strain was changed to *Streptomyces albulus* subsp. lysinopolymerus No.346-D strain, εPL was produced and its concentration was determined by the same method as in Example 5.

The yield of εPL per liter of the culture solution was 0.16 gr.

EXAMPLE 6

To 1.5 liter of the culture medium containing the same component as that of the first culture medium described in Example 1, 0.05 volume % of an defoaming agent of a polyoxyalkylene glycol derivative was added. The culture solution 50 ml in which the mutant 11011A-1 strain tolerant to S-aminoethyl-L-cysteine was precultivated was inoculated in the said medium, and the mutant was cultivated with shaking of 600 rpm at 30° C. in an air flow rate of 2 l/min.

After 24 hours, 5% of glucose and 1% of ammonium sulfate were added to the medium under sterile conditions. After reducing the pH, 6N of sodium hydroxide was added while the pH was automatically and continuously controlled with a pH controller so as not to fall below 4.0. After the cultivation, the bacteria were removed with a centrifuge and εPL in the culture solution was purified with an anion exchange resin of IRA-402, a cation exchange resin of IRC-50 and active carbon of Carboraffin 50 w, and the purity of the obtained εPL was 99.9 weight % and the yield of εPL per liter of the culture solution was 4.77 gr.

COMPARISON EXAMPLE 3

Using the same method as described in Example 6 except that the mutant 11011A-1 strain tolerant to S-aminoethyl-L-cysteine was changed to *Streptomyces albulus* subsp. lysinopolymerus No.346-D strain, εPL was produced. The purity of the obtained εPL was 97.8 weight % and the yield of εPL per liter of the culture solution was 0.56 gr.

EXAMPLE 7

To 1.5 liter of the culture medium containing the same component as that of the first culture medium described in Example 1, 0.05 volume % of a defoaming agent of a polyoxyalkylene glycol derivative was added. 50 ml of the culture solution in which the chloramphenicol-treated mutant strains 50833 were precultivated was inoculated in the said medium, and the mutant was cultivated with aeration and stirring at 30° C. for eight days. When the pH of the culture solution began to lower, 2.5% of glucose and 0.5% of L-lysine monohydrochloride were added to the medium under sterile conditions. Thereafter, so as not to lower the glucose concentration of the culture solution below 2%, 2.5% of glucose was sterility added successively. After reducing the pH, 6N of sodium hydroxide was added while the pH was automatically and continuously controlled with a pH controller so as not to fall below 4.0.

After the cultivation, the bacteria were removed with a centrifuge and the concentration of εPL in the culture solution was determined by the method Itzhaki. The yield of εPL per liter of the culture solution was 20.3 gr.

COMPARISON EXAMPLE 4

Using the same method as described in Example 7 except that the chloramphenicol-treated mutant 50833 strain was changed to *Streptomyces albulus* subsp. lysinopolymerus No.346-D strain, the concentration of εPL was determined by the same method as in Example 7.

The yield of εPL per liter of the culture solution was 0.20 gr.

EXAMPLE 8

To 1.5 liter of the culture medium containing the same component as that of the first culture medium described in Example 1, 0.05 volume % of a defoaming agent of a polyoxyalkylene glycol derivative was added. 50 ml of the culture solution in which the chloramphenicol-treated mutant 50833 strain was precultivated was inoculated in the said medium, and the mutant was cultivated with shaking of 600 rpm at 30° C. in an air flow rate of 2 l/min.

After 24 hours, as the pH of the culture solution began to fall, a glucose solution and a L-lysine solution were passed through the culture tank so as to maintain the concentrations of 1% of glucose and 0.2% of L-lysine, and exhausted the culture solution. After the pH was dropped, 6N of sodium hydroxide was added while the pH was automatically and continuously controlled with a pH controller so as not to fall below 4.0.

After the cultivation, the bacteria were removed with a centrifuge, and εPL in the culture solution was purified with an anion exchange resin of IRA-402, a cation exchange resin of IRC-50 and active carbon of Carboraffin 50w. Then εPL was crystallized with alcohol. The purity of the obtained εPL was 99.9 weight % and the yield was 5.02 gr.

We claim:

1. A biologically pure culture, capable of mass-producing epsilon-poly-L-lysine in an aqueous nutrient medium containing assimilable sources of carbon, nitrogen and inorganic substances, having all of the identifying characteristics of *Streptomyces albulus* subsp. lysinopolymerus 50833 FERM BP-1110.

2. A biologically pure culture, capable of massproducing epsilon-poly-L-lysine in an aqueous nutrient medium containing assimilable sources of carbon, nitrogen and inorganic substances, having all of the identifying characteristics of *Streptomyces albulus* subsp. lysinopolymerus 11011A-1FERM BR-1109.

* * * * *